US008828691B2

(12) United States Patent
Goswami et al.

(10) Patent No.: US 8,828,691 B2
(45) Date of Patent: Sep. 9, 2014

(54) PROCESS FOR RESOLVING CYCLOPROPYL DIESTERS

(71) Applicant: Bristol-Myers Squibb Company, Princeton, NJ (US)

(72) Inventors: Animesh Goswami, Plainsboro, NJ (US); Zhiwei Guo, Franklin Park, NJ (US); Yuping Qiu, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/770,219

(22) Filed: Feb. 19, 2013

(65) Prior Publication Data

US 2013/0224812 A1    Aug. 29, 2013

Related U.S. Application Data

(60) Provisional application No. 61/602,811, filed on Feb. 24, 2012.

(51) Int. Cl.
*C12P 7/62* (2006.01)
*C12P 41/00* (2006.01)

(52) U.S. Cl.
CPC .. *C12P 7/62* (2013.01); *C12P 41/00* (2013.01)
USPC ............................ 435/135; 435/132; 435/136

(58) Field of Classification Search
None
See application file for complete search history.

(56) References Cited

U.S. PATENT DOCUMENTS

2013/0096339 A1* 4/2013 Asuma et al. ................. 560/124

FOREIGN PATENT DOCUMENTS

WO    WO 2011/102388    * 8/2011

OTHER PUBLICATIONS

Alupei et al Macromolecular Rapid Comm. (2001) 22(16) 1349-1353.*
Alupei, V. et al., "Cyclodextrins in Polymer Synthesis: Synthesis and Influence of Methylated β-Cyclodextrin on the Radical Polymerization Behavior of 1,1-Disubstituted 2-Vinylcyclopropane in Aqueous Medium", Macromol. Rapid Commun., vol. 22, No. 16, pp. 1349-1353 (2001).
Cativiela, C. et al., "A Simple Synthesis of (−)-(1S,2R)-Allocoronamic Acid in Its Enantiomerically Pure Form", Tetrahedron: Asymmetry, vol. 6, No. 1, pp. 177-182 (1995).
Chen, C.-S. et al., "Quantitative Analyses of Biochemical Kinetic Resolutions of Enantiomers", J. Am. Chem. Soc., vol. 104, No. 25, pp. 7294-7299 (1982).
Den Besten, I.E. et al., "Synthesis of Ethyl 2-Vinylcyclopropane-1-carboxylate via Half-Ester Decarboxylation", Journal of Chemical and Engineering Data, vol. 15, No. 3, pp. 453-454 (1970).
Fliche, C. et al., "Enantioselective Synthesis of (1R,2S) and (1S,2S) Dehydrocoronamic Acids", Synthetic Communications, vol. 24, No. 20, pp. 2873-2876 (1994).
Jiménez, J.M. et al., "Enantioselective Total Syntheses of Cyclopropane Amino Acids: Natural Products and Protein Methanologs", Tetrahedron: Asymmetry, vol. 7, No. 2, pp. 537-558 (1996).
Lowe, D.A. et al., "Enzymatic Hydrolysis of Penicillin V to 6-Aminopenicillanic Acid by *Fusarium oxysporum*", Biotechnology Letters, vol. 8, No. 3, pp. 151-156 (1986).
Weinstock, J., "A Modified Curtius Reaction", Journal of Organic Chemistry, vol. 26, p. 3511 (1961).
Wheeler, T.N. et al., "A Convenient and Efficient Synthesis of 1-Aminocyclopropanecarboxylic Acid (ACC)", Synthetic Communications, vol. 18, No. 2, pp. 141-149 (1988).
Wirz, B. et al., "Enzymatic preparation of homochiral 2-isobutyl succinic acid derivatives", Tetrahedron: Asymmetry, vol. 8, No. 2, pp. 187-189 (1997).

* cited by examiner

*Primary Examiner* — Nashaat Nashed
(74) *Attorney, Agent, or Firm* — Pamela A. Mingo

(57) ABSTRACT

The present disclosure provides a method for the stereospecific hydrolysis of racemic 1,1-dialkyloxycarbonylcyclopropanes.

8 Claims, No Drawings

PROCESS FOR RESOLVING CYCLOPROPYL DIESTERS

CROSS-REFERENCE TO RELATED APPLICATIONS

This application claims the benefit of U.S. Provisional Application Ser. No. 61/602,811 filed Feb. 24, 2012.

The present disclosure provides a method for the stereospecific hydrolysis of racemic 1,1-dialkyloxycarbonylcyclopropanes.

Trans-(1R,2S)-1-tert-butoxycarbonylamino-1-carboxy-2-vinylcyclopropane (1) is an important chiral intermediate for the synthesis of certain Hepatitis C Virus protease inhibitors.

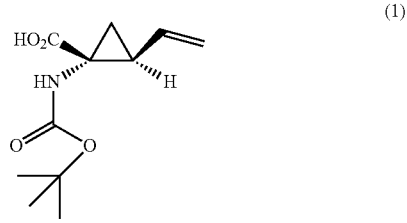 [SMILES: C=C[C@@H]1C[C@]1(NC(=O)OC(C)(C)C)C(=O)O]

Different synthetic approaches have been reported. Fliche, et al. report a chemoenzymatic route, which involves enzymatic resolution of the racemic dimethyl ester (2) to prepare the corresponding monoacid cis-(1S,2S)-(6a) followed by chemical conversion of (6a) to the desired chiral intermediate (1) (Scheme 1).

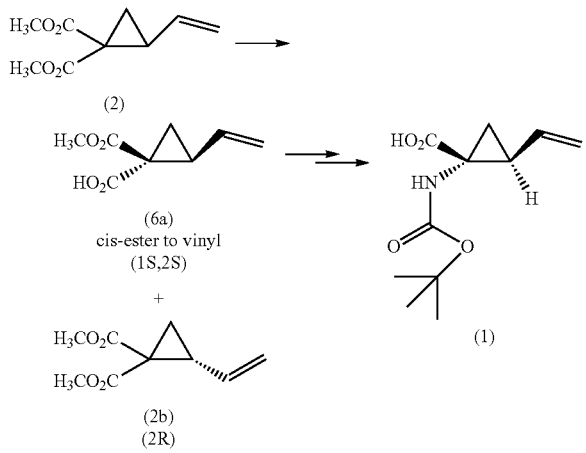

In this approach, all the enzymes evaluated showed only moderate enantioselectivity and even with the best enzyme the enzymatic resolution had to be carried out twice to improve the ee to a level necessary for practical application for the enantioselective synthesis of pharmaceutical intermediates. Enzymatic hydrolysis of the racemic methyl ester (2) by Carboxyl Naproxen esterase (CENP) gave the monoacid cis-(1S,2S)-(6a) with ee of only 70% and unreacted starting material enriched with the dimethyl ester (2R)-(2b) with ee 95%. The monoacid cis-(1S,2S)-(6a) ee 70% was re-esterified to the diester, and a second enzymatic hydrolysis with CENP improved the ee of the monoacid cis-(1S,2S)-(6a) to 90%. A second enzymatic hydrolysis of the enriched dimethyl ester (2R)-(2b) ee 95% by Esterase 30000 provided the monoacid cis-(1R,2R)-(6a) with an ee 95%.

Porcine liver estearase (PLE) catalyzed hydrolysis of the diethyl ester (±)-(3) was also reported to give the monoacid (7a) with low diastereoselectivity (de 60%). Non-enzymatic hydrolysis of the diethyl ester (±)-(3) showed partial diastereo-preference to give racemic cis-(±)-(7) as the major product.

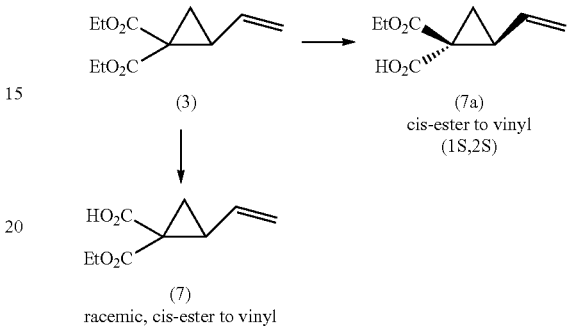

Examples such as these highlight the need to find an enzyme with high diastereo- and high enantioselectivity for the practical, enantioselective synthesis of pharmaceutical intermediates such as vinylcyclopropane (1).

In a first aspect the present disclosure provides a process for preparing a compound of formula (II)

wherein
$R^1$ is alkyl; and
$R^2$ is selected from alkenyl and alkyl;
the process comprising:
reacting a compound of formula (I)

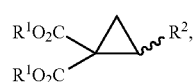

with an enzyme.

In a first embodiment of the first aspect the enzyme is a hydrolytic enzyme. In a second embodiment of the first aspect the hydrolytic enzyme is selected from lipase, esterase, protease, and amidase. In a third embodiment of the first aspect the enzyme is selected from Esterase from *Bacillus subtilis*, Penicillin V Amidohydrolase, and Protease from *Aspergillus oryzae*. In a fourth embodiment of the first aspect the enzyme is Penicillin V Amidohydrolase. In a fifth embodiment of the first aspect the Penicillin V amidohydralase is from *Fusarium oxysporum*. In a sixth embodiment of the first aspect the Penicillin V amidohydrolase enzyme is obtained from a recombinant organism containing the Penicillin V amidohydrolase gene of *Fusarium oxysporum*.

In a seventh embodiment of the first aspect $R^1$ is alkyl wherein the alkyl is selected from methyl, ethyl, propyl, and butyl. In an eighth embodiment of the first aspect $R^2$ is $C_2$alkenyl.

In a ninth embodiment of the first aspect the compound of formula (II) is obtained with a diastereomeric excess equal to or greater than 90%. In a tenth embodiment of the first aspect the compound of formula (II) is obtained with a diastereomeric excess of 95% and higher. In an eleventh embodiment of the first aspect the compound of formula (II) is obtained with an enantiomeric excess of more than 70%. In a twelfth embodiment of the first aspect the compound of formula (II) is obtained with an enantiomeric excess of 90% and higher. In a thirteenth embodiment of the first aspect the compound of formula (II) is obtained with an enantiomeric excess of 95% and higher.

Other embodiments of the present disclosure may comprise suitable combinations of two or more of embodiments and/or aspects disclosed herein.

Yet other embodiments and aspects of the disclosure will be apparent according to the description provided below.

The enzymes can be used as such or as immobilized enzymes. In addition, the enzymes as such or in the immobilized form can be reused.

As used in the present specification, the following terms have the meanings indicated:

The term "alkenyl," as used herein, refers to a straight or branched chain group of two to six carbon atoms containing at least one carbon-carbon double bond.

The term "alkyl," as used herein, refers to a group derived from a straight or branched chain saturated hydrocarbon containing from one to six carbon atoms.

All of the processes in the present disclosure can be conducted as continuous processes. The term "continuous process," as used herein, represents steps conducted without isolation of the intermediate.

The structures of the relevant compounds are shown in Schemes 3-5.

The abbreviations used in the present application, including particularly in the illustrative schemes and examples which follow, are well-known to those skilled in the art. Some of the abbreviations used are as follows: TFA for trifluoroacetic acid; min for minutes; h for hours; DMSO for dimethylsulfoxide; MTBE for methyl tert-butyl ether; Et for ethyl; n-Pr for n-propyl, n-Bu for n-butyl, t-Bu for tert-butyl; and Me for methyl.

EXAMPLES

Scheme 3

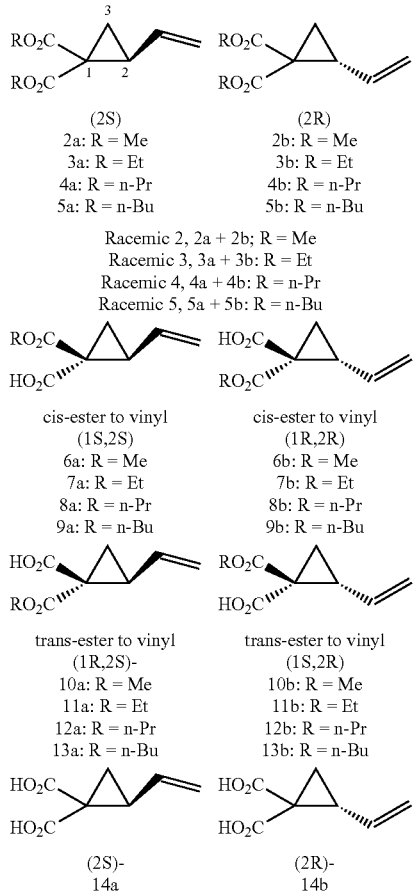

The cis- and trans- isomers were shown with different compound numbers.
The enantiomers were identified as a and b of same number (1, 2, 3, 4).
The cis- and trans- in the text represents the relation between the vinyl and ester group.

Scheme 4

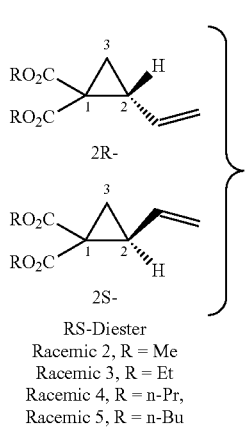

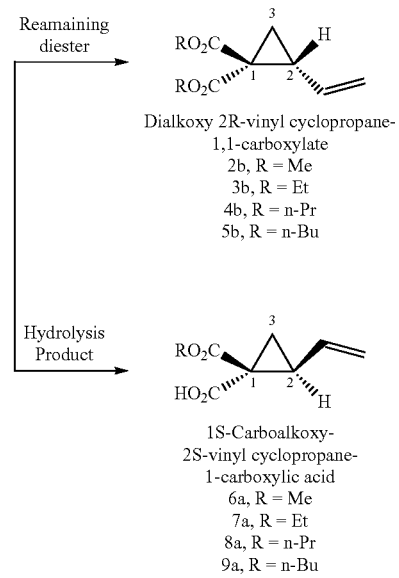

Scheme 5

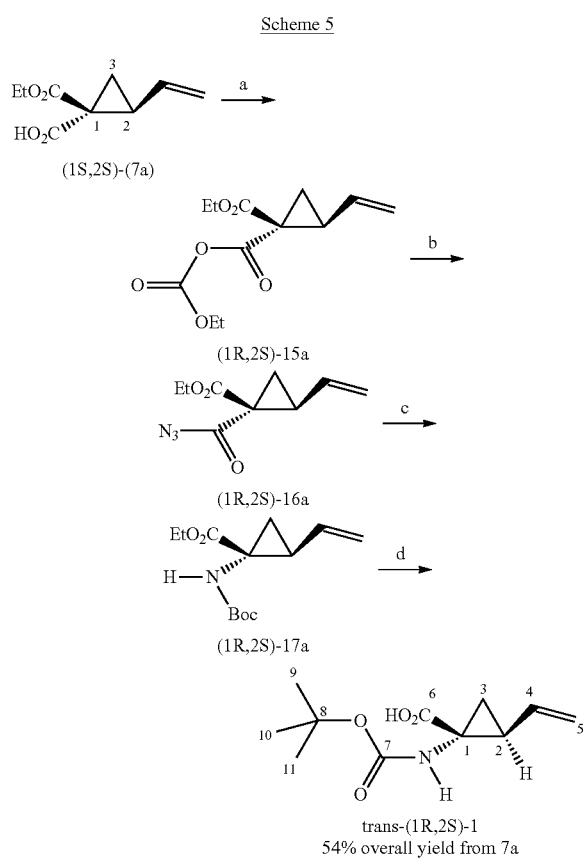

a. ClCO₂Et, Et₃N; b. NaN₃, water; c. t-BuOH, reflux; d. LiOH, water.
Prefix trans- represents the relationship between N—Boc and vinyl groups in 17a and 1.

Chemicals were purchased from VWR and/or Aldrich. NMR spectra were recorded in CDCl₃ (except as indicated) on a BRUKER-300 and/or a JEOL-400 NMR spectrophotometer. The proton assignments were based upon $^1$H-$^1$H COSY experiments. LCMS data were recorded on a Shimadzu LCMS system with positive ion electrospray (ES+) or negative ion electrospray (ES−) methods. Rotation data were recorded on a Perkin-Elmer 241 Polarimeter.

Reversed phase HPLC achiral method 1, and chiral methods 2 and 3 were performed with various gradients of solvent A (0.05% TFA in water:methanol 80:20) and solvent B (0.05% TFA in acetonitrile:methanol 80:20) at ambient temperature with UV detection at 210 nm except where indicated otherwise. Normal phase HPLC method 4 was for chiral analysis. Some modifications of these HPLC methods were also used during the study for better separation or faster analysis. Method-1 was used for achiral analysis of all compounds and performed on a YMC-Pack Pro C18 column (3 μm, 150×4 6 mm) with a flow rate of 1 mL/min and a gradient from 30% to 100% solvent B over 14 min and holding 100% B for additional 2 min. The retention times were 6.1, 8.7, 11.4 and 13.5 min for the diesters 2, 3, 4 and 5; 4.2, 5.3, 6.7 and 8.1 min for the cis-monoacids 6, 7, 8 and 9; 4.0, 5.1, 6.5 and 7.9 min for the trans-monoacids 10, 11, 12 and 13; 3.0 min for the diacid 14; 8.7 and 12.5 min for the trans-compound 17 and its cis-isomer 18; 5.9 min for the trans-compound 1 respectively.

Method-2 was used for chiral analysis of the trans-compound 17 and was performed on a Chiralcel OD-RH column (150×4.6 mm) with a flow rate of 0.5 mL/min and an isocratic composition of 35% solvent B for 25 min. The retention times were 19.1 min for (1R,2S)-17a and 20.6 min for (1S,2R)-17b.

Method-3 was used for chiral analysis of the trans-compound 1 and was performed on a Chiralpak AS-RH column (150×4.6 mm) with a flow rate of 0.5 mL/min and an isocratic composition of 22% solvent B for 20 min. The retention times were 9.1 min for (1R,2S)-1 and 11.6 min for its enantiomer (1S,2R)-1b.

Method-4 was used for chiral analysis of the cis-monoacids 6 to 9 and was performed on a Chiralpak AD-H column (250×4 6 mm) with a flow rate of 1 mL/min and an isocratic composition of 5% isopropanol in heptane for 15 min. The retention times were 8.0 and 8.7 min for 6b and 6a; 7.4 and 8.2 min for 7b and 7a; 6.9 and 7.6 min for 8b and 8a; 6.6 and 7.0 min for 9b and 9a respectively.

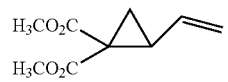

Synthesis of Racemic Dimethyl Ester (2)

To a 250 mL flask were added (E)-1,4-dibromo-2-butene (92.6316 mmol, 20.014 g), potassium carbonate (anhydrous, 231.802 mmol, 32.036 g), methanol (anhydrous, 100 mL), and dimethyl malonate (101.8786 mmol, 13.4598 g). The reaction was exothermic in the beginning. The mixture was stirred at ambient temperature for 20 h. The solvent was removed under reduced pressure. The residue was treated with 200 mL of ethyl acetate and 200 mL of water. The organic layer was further washed with water (2×100 mL), dried over MgSO₄, filtered. Solvent removal of the filtrate gave dimethyl ester (2) (14.7833 g, 86.6% yield). Pure analytical sample was obtained by distillation (89° C./5 mmHg). $^1$H NMR (CDCl₃) δ 5.43-5.36 (m, 1H), 5.26 (apparent d, J=16.7 Hz, 1H), 5.10 (apparent d, J=10.4 Hz, 1H), 3.703 (s, 3H), 3.700 (s, 3H), 2.55 (apparent q, J=8.5 Hz, 1H), 1.68 (dd, J=7.63, 4.88 Hz, 1H), 1.55 (dd, J=9.16, 4.89 Hz, 1H) ppm. $^{13}$C NMR (CDCl₃) δ 170.01, 167.78, 133.05, 118.65, 52.68, 52.53, 35.81, 31.43, 20.58 ppm.

Synthesis of Racemic Diethyl Ester (3)

To a 250 mL flask were added (E)-1,4-dibromo-2-butene (92.63 mmol, 20.01 g), potassium carbonate (anhydrous, 231.44 mmol, 31.99 g), ethanol (100 mL), and diethyl malonate (102.00 mmol, 16.34 g). The mixture was stirred at ambient temperature for 46 h. The same work up procedure used to prepare the dimethyl ester gave diethyl ester (3) (20.473 g, 104% yield). Pure analytical sample was obtained by distillation (97° C./5 mmHg). $^1$H NMR (CDCl₃) δ 5.47~5.40 (m, 1H), 5.29 (apparent d, J=17.09 Hz, 1H), 5.13 (apparent d, J=10.1 Hz, 1H), 4.26-4.12 (m, 4H), 2.56 (apparent q, J=8.24 Hz, 1H), 1.68 (dd, J=7.33, 4.89, 1H), 1.54 (dd, J=9.16, 4.89 Hz, 1H), 1.28~1.23 (m, 6H) ppm. $^{13}$C NMR (CDCl₃) δ 169.69, 167.44, 133.27, 118.39, 61.62, 61.44, 36.04, 31.08, 20.35, 14.23, 14.11 ppm.

Synthesis of Racemic Dipropyl Ester (4)

To a 250 mL flask were added (E)-1,4-dibromo-2-butene (92.598 mmol, 20.007 g), potassium carbonate (anhydrous, 231.668 mmol, 32.018 g), 1-propanol (100 mL), and dipropyl malonate (101.916 mmol, 19.183 g). The mixture was stirred at 60° C. for 24 h. The same work up procedure used to prepare the dimethyl ester gave dipropyl ester (4) (23.069 g, 103.7% yield). $^1$H NMR (CDCl$_3$) δ 5.47~5.40 (m, 1H), 5.28 (apparent d, J=17.09 Hz, 1H), 5.12 (apparent d, J=10.38 Hz, 1H), 4.15~4.03 (m, 4H), 2.57 (apparent q, J=8.24 Hz, 1H), 1.70-1.62 (m, 5H), 1.54 (dd, J=8.85, 4.88, 1H), 0.95-0.92 (apparent t, J=7.33 Hz, 6H) ppm. $^{13}$C NMR (CDCl$_3$) δ 169.82, 167.57, 133.35, 118.40, 67.26, 67.20, 36.16, 31.13, 22.04, 21.97, 20.47, 10.42, 10.35 ppm.

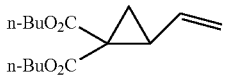

Synthesis of Racemic Dibutyl Ester (5)

To a 250 mL flask were added (E)-1,4-dibromo-2-butene (92.784 mmol, 20.047 g), potassium carbonate (anhydrous, 231.430 mmol, 31.985 g), 1-butanol (100 mL), and dibutyl malonate (101.869 mmol, 22.032 g). The procedure used to prepare the dimethyl ester gave dibutyl ester (5) (23.933 g, 96.1% yield). $^1$H NMR (CDCl$_3$) δ 5.42 (m, 1H), 5.27 (apparent d, J=16.78 Hz, 1H), 5.10 (apparent d, J=10.37 Hz, 1H), 4.17-4.05 (m, 4H), 2.54 (apparent q, J=8.54 Hz, 1H), 1.66 (dd, J=7.63, 4.88 Hz, 1H), 1.62-1.56 (m, 4H), 1.52 (dd, J=8.85, 4.89 Hz, 1H), 1.40-1.32 (m, 4H), 0.93-0.89 (m, 6H). $^{13}$C NMR (CDCl$_3$) δ 169.80, 167.55, 133.33, 118.34, 65.51, 65.37, 36.12, 34.96, 31.09, 30.69, 30.63, 20.44, 19.10, 13.65, 13.63 ppm.

Enzyme Screening

Multiwell plates containing enzymes were taken out from the cold room. Each well contained about 10 mg lyophilized or immobilized enzyme. Phosphate buffer, 100 mM, pH 7 (1 mL) was added to each well. The plates were shaken in the Thermomixer Rat 600 rpm at 28° C. for 5 minutes. A solution of 1 μL (1.097 mg) of the racemic dimethyl ester (±)-(2) in 20 μL DMSO was added to each well. The hydrolysis was carried out by shaking in the same shaker at 600 rpm and 28° C. for 24 h. After 24 h, acetonitrile (1 mL) was added to each well. The mixtures were placed in the shaker at 300 rpm at room temperature for 10 minutes for mixing and then filtered through a 0.2μ filter and analyzed by reversed phase HPLC (Method 1) to determine the extent of hydrolysis. The reaction mixtures from the hydrolysis of enzymes showing more than 10% conversion were analyzed by chiral HPLC to determine the enantiomeric compositions. To the reaction mixture from enzymatic hydrolysis, 0.1 mL of 1 N HCl was added to make the mixture acidic (pH~2.5) and extracted with 2 mL ethyl acetate. Ethyl acetate layer was separated and evaporated with a stream of nitrogen. The residue was dissolved in heptane-isopropanol (95:5, 1 mL) and analyzed by chiral HPLC (Method 4).

TABLE 1

Results of Enzymatic Hydrolysis Screening

| Enzyme | Source | Supplier | Reversed Phase HPLC-Area Ratio | | | Chiral HPLC* | |
|---|---|---|---|---|---|---|---|
| | | | trans- (10a + 10b) | cis- (6a + 6b) | Diester (2a + 2b) | 1$^{st}$ Peak (1R,2R)- 6b | 2$^{nd}$ Peak (1S,2S)- 6a |
| Esterase BS1 | Bacillus subtilis | Julich | 9% | 70% | 20% | 12.4% | 87.6% |
| Esterase BS2 | Bacillus subtilis | Julich | 51% | 48% | 1% | 13.1% | 86.9% |
| Acylase I | Porcine Kidney | Sigma | 29% | 48% | 23% | 57.2% | 42.8% |
| Porcine Liver Esterase | Porcine Liver | Sigma | 19% | 81% | 0% | 56.2% | 43.8% |
| Lipase OF | Candida rugosa | Sepracor | 19% | 47% | 34% | 72.0% | 28.0% |
| Esterase 30000 | Bacterial Origin | Gist Brocades | 17% | 57% | 26% | 91.5% | 8.5% |
| Lipase | Mucor miehei | Sigma | 5% | 28% | 67% | 94.3% | 5.7% |
| Chirazyme, L-3, Lyo | Candida rugosa | Boehringer | 21% | 31% | 48% | 54.6% | 45.4% |
| Lipase OF | Candida cyllindracea | Meito Sangyo | 26% | 70% | 4% | 59.6% | 40.4% |
| Lipase N | Rhizopus niveus | Amano | 0% | 9% | 91% | 93.9% | 6.1% |
| Subtilisin Carlsberg | Bacillus globigii | Sigma | 11% | 89% | 0% | 53.8% | 46.2% |
| ChiroCLE C-BL | Bacillus licheniformis | Altus | 8% | 66% | 26% | 52.8% | 47.2% |

TABLE 1-continued

Results of Enzymatic Hydrolysis Screening

| Enzyme | Source | Supplier | Reversed Phase HPLC-Area Ratio | | | Chiral HPLC* | |
|---|---|---|---|---|---|---|---|
| | | | trans-(10a + 10b) | cis-(6a + 6b) | Diester (2a + 2b) | $1^{st}$ Peak (1R,2R)-6b | $2^{nd}$ Peak (1S,2S)-6a |
| Chirazyme P1 | Bacillus licheniformis | Boehringer | 5% | 38% | 57% | 53.9% | 46.1% |
| Seaprose S | Aspergillus oryzae | Amano | 33% | 67% | 0% | 71.9% | 28.1% |
| Protease | Bacillus licheniformis | Sigma | 6% | 42% | 52% | 54.4% | 45.6% |
| Protease | Bacillus sp | Sigma | 0% | 30% | 70% | 61.2% | 38.8% |
| Protease P "Amano" 6 | Aspergillus melleus | Amano | 30% | 61% | 9% | 71.8% | 28.2% |
| Pen V Amidase | Fusarium oxysporum | BMS** | 0% | 73% | 27% | 8.9% | 91.1% |
| Protease, Type XIV | Streptomyces griseus | Sigma | 4% | 38% | 58% | 82.2% | 17.8% |
| Protease M | Aspergillus oryzae | Amano | 6% | 50% | 44% | 22.0% | 78.0% |

*Assignment of the HPLC peaks was confirmed by conversion of (6a) to the known compound (1).
**Pen V amidase from *Fusarium oxysporum* is an immobilized recombinant penicillin V amidohydrolase originally used for enzymatic hydrolysis of penicillin V to 6-aminopenicillanic acid and made in-house by Bristol-Myers Squibb (see U.S. Pat. Ser. No. 5,516,679 and Lowe, D. et al. *Biotechnol. Lett.* 1986, 8, 151-156).
+PS Enzymatic Hydrolysis of the Diethyl Ester (±)-3 with Pen V Amidase to Prepare cis-(1S,2S)-(7a)

The reaction was carried out in a jacketed 2 L flask on a pH STAT to maintain the temperature at 30° C. and pH 8.0 by automatic addition of 1 M aqueous NaOH. To the flask was charged 60 g of Pen V amidase and 1.5 L of 0.1 M phosphate buffer pH 8.0. Under stirring, the diethyl ester (±)-(3) (30.5 g) was added. After 48 h, the rate of NaOH consumption indicated the completion of hydrolysis. The reaction was terminated by filtering the mixture to remove the enzyme. The solid was washed with 0.1 M phosphate buffer, pH 8.0 (200 mL) and ethyl acetate (3×200 mL). The filtrate and washings were combined and two phases were separated. The aqueous phase was further extracted with ethyl acetate (2×600 mL). The combined organic phase was washed with 300 mL of 5% NaHCO$_3$, 300 mL of water. Solvent removal at room temperature gave 16.7 g of the remaining diethyl ester (2R)-(3b), isolated yield 55%, AP 97, $[\alpha]_D$=+23.98 (c=2.16, CHCl$_3$). NMR (CDCl$_3$) $^1$H δ 5.46 (m, 1H), 5.30 (dd, 1H), 5.14 (dd, 1H), 4.19 (m, 4H), 2.58 (q, 1H), 1.69 (m, 1H), 1.56 (m, 1H), 1.27 (two triplets, 6H) ppm.

The aqueous phase was acidified with 4 M HCl and extracted with ethyl acetate (3×600 mL). The organic extracts were combined and washed with water. Solvent removal in a rotary evaporator at 20-25° C. gave 10.3 g product cis-(1S,2S)-(7a), isolated yield 39%, AP 98, de 99% and ee 90%, $[\alpha]_D$=+ 5.52 (c=2.82, CHCl$_3$). NMR (CDCl$_3$) $^1$H δ 11.35 (broad, 1H), 5.68 (m, 1H), 5.43 (d, J=16.9 Hz, 1H), 5.25 (d, J=10.1 Hz, 1H), 4.30 (m, 2H), 2.75 (q, J=8.6 Hz, 1H), 1.95 (m, 2H), 1.32 (t, J=7.1 Hz, 3H) ppm.

Modified Curtius Reaction Converting cis-(1S,2S)-(7a) to trans-(1R,2S)-(17a)

To a solution of cis-(1S,2S)-(7a) (3.684 g, de 99%, ee 90%) in acetone (50 mL, dried over molecular sieve) at −5 to 0° C. was added triethylamine (3.35 mL) followed by dropwise addition of a solution of ethyl chloroformate (2.49 mL) in 10 mL dry acetone. After 30 min at −5 to 0° C., the mixture was stirred at room temperature for 18 h. The white precipitate formed was removed by filtration. The filtrate was cooled to −5° C. and a solution of sodium azide (1.95 g) in 10 mL of water was added dropwise. The mixture was stirred at −5 to 0° C. for 1 h. To the mixture was added 100 mL of cold (5° C.) water. The mixture was extracted with MTBE (3×80 mL). The MTBE phase was dried over MgSO$_4$, filtered. Solvent removal in a rotary evaporator at 20-25° C. gave 4.118 g light yellow azide (16a), overall yield 98%.

A mixture of the azide (16a) in 50 mL of anhydrous t-butanol was refluxed for 18 h (100° C. oil bath). The mixture was concentrated to dryness under reduced pressure to give 4.259 g light yellow product trans-(1R,2S)-(17a), AP 78, de>99%, ee 90%, overall yield 83% from (7a).

Hydrolysis of Trans-(1R,2S)-(17a) to Trans-(1R,2S)-(1)

A mixture of the crude (17a) obtained in the last section, 10 mL of THF and 40 mL of aqueous 2 M LiOH was stirred at room temperature for 5 days. The mixture was extracted with 100 mL of MTBE. The MTBE phase was back extracted with 20 mL of water. The combined aqueous phase was acidified with a mixture of KHSO$_4$ (10.9 g) and water (30 mL), and extracted with ethyl acetate (2×100 mL). The combined ethyl acetate extract was washed with brine (2×50 mL), water (2×50 mL), dried over MgSO$_4$, and filtered. Solvent removal at room temperature gave 3.192 g of crude product, AP 77. The crude product was subjected to flash chromatography (80 g silica gel) and eluted with heptane-ethyl acetate-acetic acid (50:50:1) to give 2.448 g (54% overall yield from (7a)) of white solid trans-(1R,2S)-(1), AP 95, ee 90%, $[\alpha]_D$+22.34 (c 1.41, MeOH). LCMS m/z 226 (M-H) by ES-method and 250 (M+Na) by ES+method. $^1$H, $^1$H-$^1$H COSY, $^{13}$C and DEPT NMR spectra of (1) were recorded in DMSO-d$_6$. The proton assignment was based upon $^1$H-$^1$H COSY and carbon assignment was based upon DEPT experiments. $^1$H δ 12.41 (broad, 1H, CO$_2$H), 7.52 (broad, 0.74H, NH of the major rotamer), 7.18 (broad, 0.26H, NH of the minor rotamer), 5.67 (m, 1H, 4-CH), 5.21 (d, J=15.8 Hz, 1H, S—CH$_2$-A), 5.02 (d, J=10.3 Hz, 1H, S—CH$_2$—B), 2.02 (m, 1H, 2-CH), 1.49 (m, 1H, 3-CH$_2$-A), 1.35 (s, 9H, Boc), 1.22 (m, 1H, 3-CH$_2$—B) ppm. $^{13}$C of the major rotamer δ 172.41 (C-6), 155.51 (C-7), 134.95 (C-4 up in DEPT), 116.78 (C-5 down in DEPT), 77.95 (C-8), 39.92 (C-1 not show in DEPT), 32.45 (C-2 up in DEPT), 28.18 (C-9, 10 and 11 up in DEPT), 22.52 (C-3 down in DEPT) ppm.

General Procedure for Enzymatic Hydrolysis in Small Vials

To each vial (4 mL) was charged Pen V Amidase (10 mg or as indicated) and 1 mL of a buffer. The vial is placed in the well of a multiwell plate and shaken in a Thermomixer shaker. After 10 min, the substrate diester (2, 3, 4 or 5) 10 μL or as indicated was added and the shaking continued. After 24 h or indicated time, 20 μL of 4 M HCl and 3 mL of acetonitrile was added. The mixture was filtered through 0.2 μm filter. 1 mL of the filtrate was subjected to HPLC method-1 for achiral analysis. The conversion was estimated by the relative HPLC area. The remaining filtrate was partially concentrated with a stream of nitrogen and extracted with ethyl acetate. The extract was dried and the residue was dissolved in isopropanol-heptane (1:1), filtered through 0.2 μm filter and subjected to HPLC method-4 for chiral analysis.

The effect of co-solvents (5-10% volume) was evaluated for the Pen V amidase catalyzed hydrolysis of (±)-(2). Straight chain alkanes such as hexane, heptanes, octane, and tetradecane improved the enantioselectivity with slight effect on the enzyme activity. Representative data are shown in Table 2:

TABLE 2

Effect of water immiscible co-solvents$^{a\cdot}$

| Co-solvent | Conversion (%) | ee (%) |
|---|---|---|
| None | 45 | 93.2 |
| Hexane | 25 | 98.0 |
| Heptane | 52$^b$ | 97.4 |
| Octane | 32 | 96.9 |
| Tetradecane | 39 | 96.0 |

$^{a\cdot}$SM (±)-(2) 20 g/L, Pen V amidase 50 g/L, co-solvent 10%, pH 7, room temperature, 24 h.
$^b$The conversion might be over estimated.

Multiple experiments were carried out with different heptanes concentrations at different pH and temperatures to evaluate the effect of Pen V amidase catalyzed hydrolysis of the dimethyl ester (±)-(2). Considering both enzyme activity and enantioselectivity, the best conditions were determined to be: aqueous buffer, pH 6.5 to 7 with about 20% volume of heptanes at 28-32° C.

Enzymatic Hydrolysis of the Dimethyl Ester (f)-(2) to Prepare cis-(1S,2S)-(6a)

The reaction was carried out in a jacketed 500 mL flask on a pH STAT to maintain the temperature at 32° C. and pH 7.0 by automatic addition of 1 M aqueous NaOH. To the flask was charged 30 g of Pen V amidase, 240 mL of 0.1 M phosphate buffer pH 7.0 and 60 mL of heptane. Under stirring, the dimethyl ester (±)-(2) (6.47 g) was added. After 22 h, analysis of a sample showed conversion of 48%. The NaOH consumption also indicated reaction completion. The whole reaction mixture was adjusted to pH 8.0 with 1 M NaOH and extracted with ethyl acetate (3×200 mL). The combined organic phase was washed with 0.1 M phosphate buffer, pH 8.0 (200 mL) and water (200 mL). Solvent removal gave 3.1 g of the remaining dimethyl ester (2R)-(2b), isolated yield 48%, AP 98, [α]$_D$+34.15 (c 1.95, CHCl$_3$). NMR (CDCl$_3$) $^1$H δ 5.38-5.49 (m, 1H), 5.30 (dd, J=17.0, 1.8 Hz, 1H), 5.15 (dd, J=10.0, 1.8 Hz, 1H), 3.75 (s, 6H), 2.60 (m, 1H), 1.73 (dd, J=7.5, 4.9 Hz, 1H), 1.59 (dd, J=9.0, 4.9 Hz, 1H) ppm. $^{13}$C δ 169.59, 167.37, 132.74, 118.29, 52.33 (2C), 35.42, 31.04, 20.20 ppm.

The aqueous phase (pH 8.0) was acidified to pH 2 with 6 N HCl immediately after extraction of the remaining unreacted diester. Extraction of the acidified aqueous phase with ethyl acetate (3×200 mL) and solvent removal gave the desired monoacid cis-(1S,2S)-(6a), 2.5 g, isolated yield 42%, AP 97, de 99% and ee 95%, [α]$_D$-8.28 (c 1.63, CHCl$_3$). NMR (CDCl$_3$) $^1$H δ 10.5 (broad, 1H), 5.6 (m, 1H), 5.39 (d, J=17.1 Hz, 1H), 5.24 (d, J=10.0 Hz, 1H), 3.81 (s, 3H), 2.73 (m, 1H), 2.0 (m, 2H) ppm. $^{13}$C δ 171.99, 170.29, 131.99, 119.56, 52.49, 35.53, 33.86, 21.86 ppm.

Non-Enzymatic Hydrolysis to Determine the ee of (2R)-(2b)

A solution of (2R)-(2b) (840 mg, 4.6 mmol) obtained from the enzymatic hydrolysis experiment described above in 5 mL of MeOH was cooled in an ice-bath. Under stirring, 330 mg of KOH (5.9 mmol) was added in three portions in 10 min. After 5 h, the reaction mixture was concentrated, mixed with 10 mL of water, extracted with ethyl acetate (3×10 mL). The aqueous phase was acidified to pH 4.5 with 1 M HCl and extracted with ethyl acetate (2×10 mL). Solvent removal of the acidic organic extract gave 272 mg of the monoacid mixture. The total AP of 98 and de of 85% were determined by achiral HPLC methods-1. The ee of cis-(1R,2R)-(6b) obtained was determined to be 82% by chiral HPLC method-4.

What is claimed is:
1. A process for preparing a compound of formula (II)

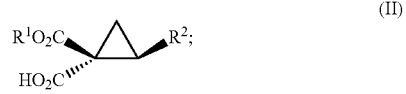

(II)

wherein
R$^1$ is alkyl; and
R$^2$ is selected from alkenyl and alkyl;
the process comprising:
contacting a compound of formula (I)

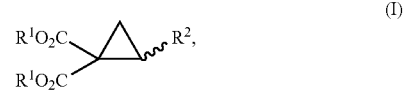

(I)

With *Fusarium oxysporum* Penicillin V Amidohydrolase.
2. The process of claim 1 where R$^1$ is alkyl wherein the alkyl is selected from methyl, ethyl, propyl, and butyl.
3. The process of claim 1 where R$^2$ is C$_2$alkenyl.
4. The process of claim 1 where the compound of formula (II) is obtained with a diastereomeric excess equal to or greater than 90%.
5. The process of claim 1 where the compound of formula (II) is obtained with a diastereomeric excess of 95% and higher.

6. The process of claim 1 where the compound of formula (II) is obtained with an enantiomeric excess of more than 70%.

7. The process of claim 1 where the compound of formula (II) is obtained with an enantiomeric excess of 90% and higher.

8. The process of claim 1 where the compound of formula (II) is obtained with an enantiomeric excess of 95% and higher.

* * * * *